(12) United States Patent
Bruna

(10) Patent No.: US 7,100,601 B2
(45) Date of Patent: Sep. 5, 2006

(54) DEVICE FOR NASAL OR ORAL SPRAYING OF A FLUID OR POWDERY PRODUCT

(75) Inventor: Pascal Bruna, Sotteville les Rouen (FR)

(73) Assignee: VALOIS S.A.S., Le Neubourg (FR)

( * ) Notice: Subject to any disclaimer, the term of this patent is extended or adjusted under 35 U.S.C. 154(b) by 56 days.

(21) Appl. No.: 10/478,848

(22) PCT Filed: Apr. 17, 2002

(86) PCT No.: PCT/FR02/01329

§ 371 (c)(1),
(2), (4) Date: Jul. 8, 2004

(87) PCT Pub. No.: WO02/085282

PCT Pub. Date: Oct. 31, 2002

(65) Prior Publication Data

US 2004/0231669 A1    Nov. 25, 2004

(30) Foreign Application Priority Data

Apr. 24, 2001    (FR) .................................. 01 05510

(51) Int. Cl.
*A61M 11/00* (2006.01)

(52) U.S. Cl. ........................... 128/200.14; 128/200.23; 128/203.14

(58) Field of Classification Search ........... 128/200.14, 128/200.16, 200.22, 200.23, 203.12, 203.14, 128/204.23

See application file for complete search history.

(56) References Cited

U.S. PATENT DOCUMENTS

| | | | | |
|---|---|---|---|---|
| 5,363,842 A | * | 11/1994 | Mishelevich et al. | .. 128/200.14 |
| 5,394,866 A | * | 3/1995 | Ritson et al. | .......... 128/200.14 |
| 5,692,492 A | * | 12/1997 | Bruna et al. | ............ 128/200.23 |
| 6,158,431 A | * | 12/2000 | Poole | ..................... 128/203.12 |
| 6,223,746 B1 | * | 5/2001 | Jewett et al. | .......... 128/203.12 |
| 6,249,717 B1 | * | 6/2001 | Nicholson et al. | .......... 700/241 |
| 6,390,088 B1 | * | 5/2002 | Nohl et al. | ............. 128/200.23 |
| 6,637,432 B1 | * | 10/2003 | Wakefield et al. | ..... 128/203.23 |
| 6,651,651 B1 | * | 11/2003 | Bonney et al. | ........ 128/200.23 |
| 6,698,421 B1 | * | 3/2004 | Attolini | .................. 128/200.14 |
| 6,736,135 B1 | * | 5/2004 | Klich | ..................... 128/200.14 |
| 6,752,145 B1 | * | 6/2004 | Bonney et al. | ........ 128/200.23 |
| 6,860,262 B1 | * | 3/2005 | Christrup et al. | ...... 128/200.23 |

FOREIGN PATENT DOCUMENTS

| | | |
|---|---|---|
| EP | 1 016 399 A2 | 7/2000 |
| FR | 2 440 021 A | 5/1980 |
| WO | WO 87/04354 * | 7/1987 |
| WO | WO 98 19647 A | 5/1998 |

* cited by examiner

*Primary Examiner*—Aaron J. Lewis
(74) *Attorney, Agent, or Firm*—Sughrue Mion, PLLC

(57) ABSTRACT

A fluid or powder nasal or oral spray device comprising a body (10), at least one fluid or powder reservoir (20) containing one or more doses of fluid or powder to be dispensed, manually actuated dispenser means (30), such as a pump or a valve, and a manual actuator element (40) adapted for actuating said dispenser means (30) to dispense doses of fluid or powder, said device being characterized in that it further comprises a securing system (50) which is mounted to move between a clutched position, in which said manual actuator element (40) co-operates with said dispenser means (30), and a declutched position, in which said manual actuator element (40) does not co-operate with said dispenser means (30), said securing system (50) being controlled by a parameterizable electronic control unit (60).

15 Claims, 4 Drawing Sheets

DEVICE FOR NASAL OR ORAL SPRAYING OF A FLUID OR POWDERY PRODUCT

The present invention relates to a fluid or powder nasal or oral spray device, and more particularly to such a device that is controlled electronically.

Currently, and in particular in certain pharmaceutical fields, there exists a need for devices for spraying fluid or powder, in particular medication, that must make it possible not only to spray individual doses of fluid or powder accurately and reproducibly, but also to perform other functions in order to guarantee safety and reliability for the treatment in progress. In particular, it is desirable for it to be possible to prevent overdosage, i.e. taking doses of medication too repetitively and at time intervals that are too short. Regular monitoring by the patient's doctor is also desirable. Such devices must also preferably be transportable and usable anywhere, in order to enable the user to follow a precise course of treatment without necessarily being forced to stay in one place, such as a hospital.

An object of the invention is thus to provide such a device that is simple and inexpensive to manufacture and to assemble.

In particular, an object of the present invention is to provide such a device that is easy to adapt to conventional dispenser devices that are in current use, without it being necessary to make major structural changes to said devices.

The present invention thus provides a fluid or powder nasal or oral spray device comprising a body, at least one fluid or powder reservoir containing one or more doses of fluid or powder to be dispensed, manually actuated dispenser means, such as a pump or a valve, and a manual actuator element adapted for actuating said dispenser means to dispense doses of fluid or powder, said device being characterized in that it further comprises a securing system which is mounted to move between a clutched position, in which said manual actuator element co-operates with said dispenser means, and a declutched position, in which said manual actuator element does not co-operate with said dispenser means, said securing system being controlled by a parameterizable electronic control unit.

Advantageously, said securing system comprises a mechanical element, such as a rod, mounted to move between a clutched position in which it mechanically connects said actuator element to a member secured to the dispenser means so that actuating said actuator element causes a dose of fluid or powder to be dispensed, and a declutched position in which there is no coupling between the actuator element and the dispenser means, so that actuating said actuator element does not cause any fluid or powder to be dispensed.

Advantageously, said actuator element is a button mounted to pivot or slide on one side of said body, said rod being disposed in said actuating button, one end of said rod co-operating with an orifice, when said rod is in the clutched position, which orifice serves to receive said member secured to the dispenser means.

Advantageously, said dispenser means are implemented in the form of a pump or of a valve, said member secured to the dispenser means being connected to the piston of the pump, or to the valve member of the valve.

Advantageously, said control unit comprises a microprocessor and power supply means.

Advantageously, said device further comprises indicator means such as a liquid crystal display (LCD) or sound alarms for informing the user of the state of the device.

Advantageously, said control unit can be parameterized remotely, in particular by means of a computer, and further comprises means for transmitting and receiving data.

Advantageously, said control unit can be parameterized to enable and to inhibit actuation of the device through a plurality of predeterminable functions.

Advantageously, said predeterminable functions comprise in particular access authorization, priming of the device, dosage of the fluid or powder contained in the reservoir, safety against overdosage, length of time of the treatment, shutting down to standby mode and coming out of standby mode, operating position, child safety and warning the patient's doctor.

Other characteristics and advantages of the present invention appear more clearly from the following detailed description of an advantageous embodiment thereof, given with reference to the accompanying drawings which are given by way of non-limiting example, and in which.

Figure 1:
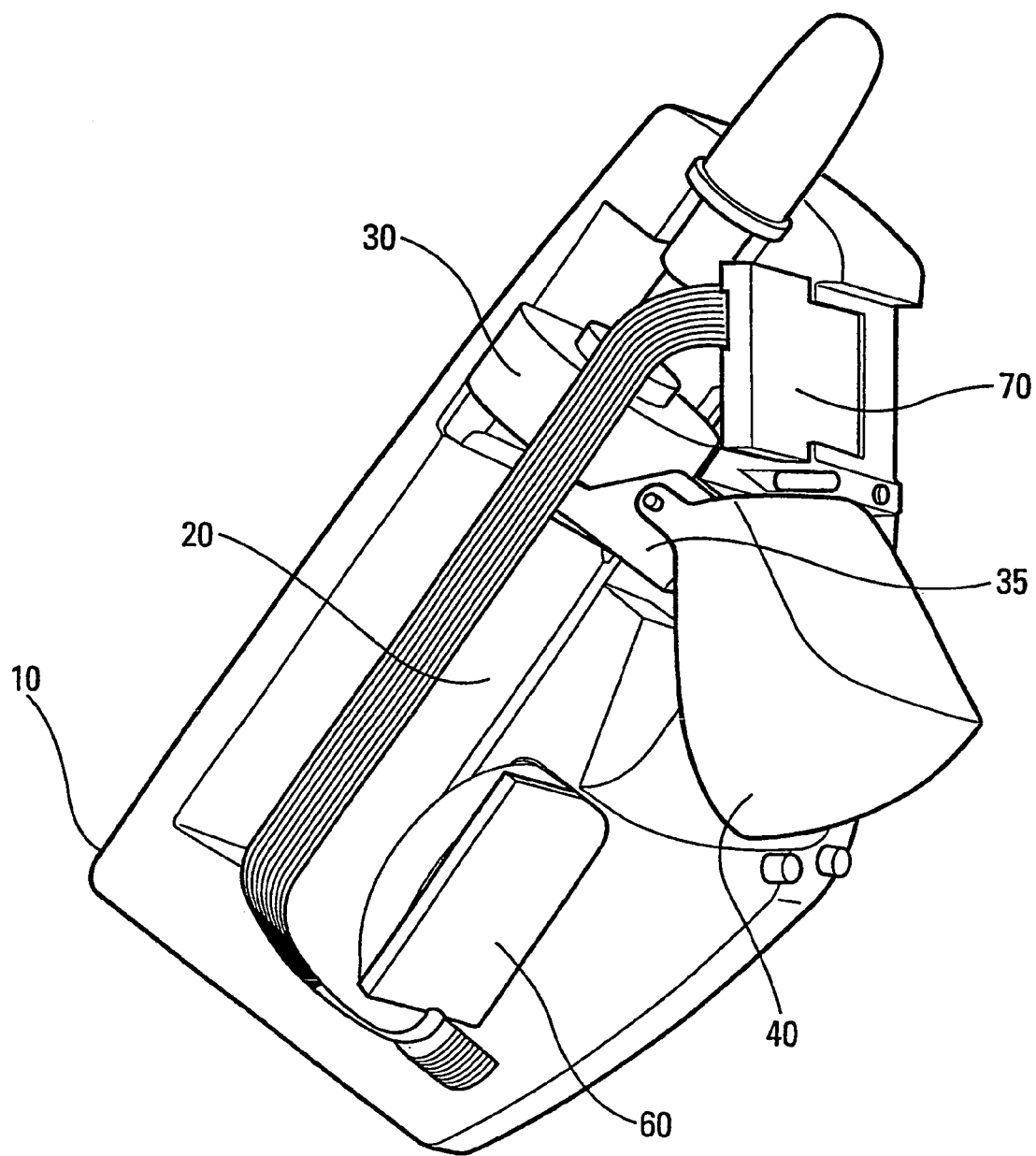
FIG. 1 is a partially cut-away diagrammatic perspective view of a spray device of the present invention.

With reference to the figures, the nasal or oral fluid or powder spray device has a body 10 which contains at least one fluid or powder reservoir 20 containing one or more doses of fluid or powder to be dispensed. In the example shown, the device includes a reservoir 20 containing a plurality of doses. Dispenser means 30, such as a pump or a valve, actuated manually by the user, are provided for selectively, accurately, and reproducibly dispensing the doses of fluid or powder contained in the reservoir 20. In the example shown in FIGS. 1 and 2A–2B, the dispenser means are implemented in the form of a pump, but other dispenser means may also be considered, such as a metering valve, or spray means that are electronic or electrical, and in particular piezoelectric. A manual actuator element 40 which is preferably implemented in the form of an actuating button slidably or pivotally mounted on one side of the body 10, and on which the user presses, is used to actuate the dispenser means 30.

In the invention, the device includes securing means 50 which are mounted to move between a clutched position, in which the manual actuator element 40 co-operates with the dispenser means 30, and a declutched position in which the manual actuator element 40 does not co-operate with said dispenser means 30. More precisely, in the clutched position, the user actuating the manual actuating button 40 causes one dose of fluid or powder to be dispensed, whereas, in the declutched position, the actuating button 40 being actuated has no effect on the dispenser means 30, and does not cause any fluid or powder to be dispensed. Manually actuating the device is thus inhibited by said securing means 50 in the declutched position. In the invention, this securing system 50 is controlled by a parameterizable electronic control unit 60. Said control unit 60, which preferably comprises a microprocessor and suitable power supply means, thus acts to move the securing system 50 between its clutched position and its declutched position.

Figure 2A:
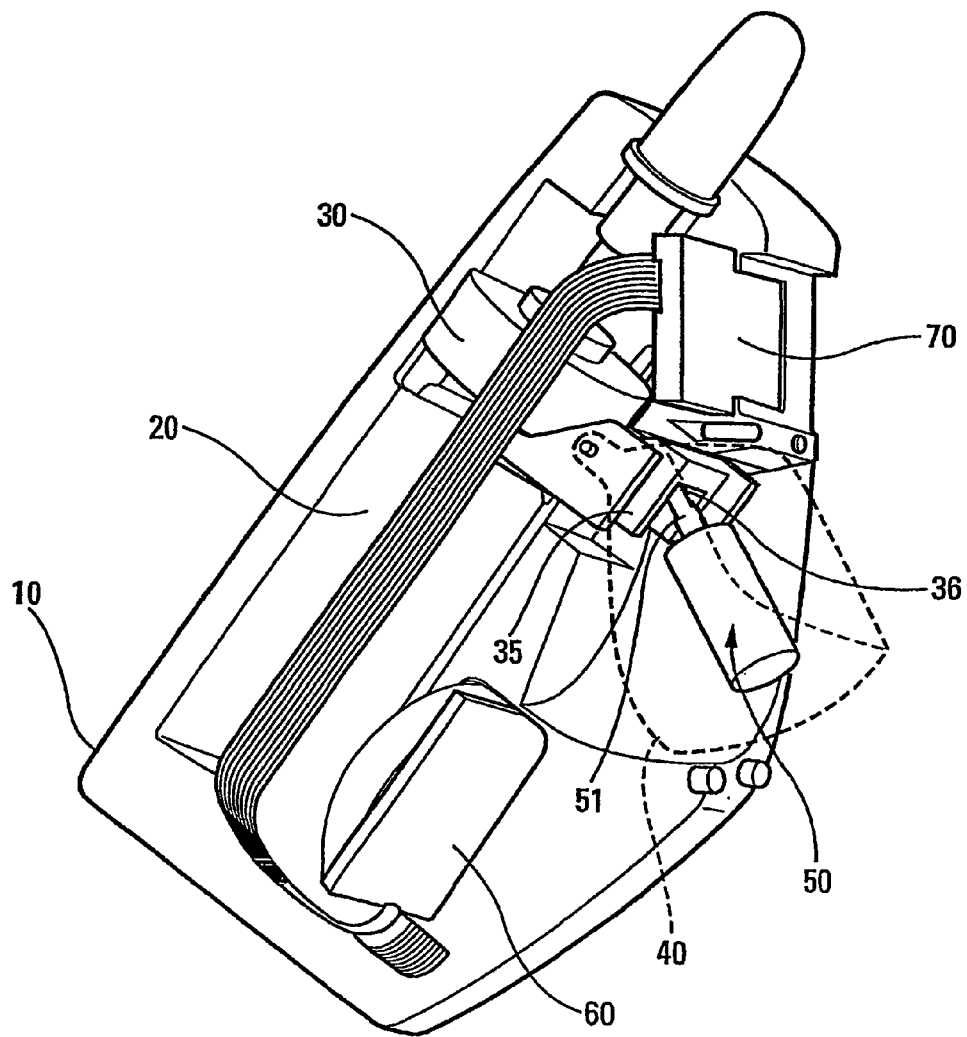
FIGS. 2A and 2B are views similar to FIG. 1, showing more precisely the securing means of an embodiment of the present invention in the clutched position and declutched position, respectively.
Figure 2B:
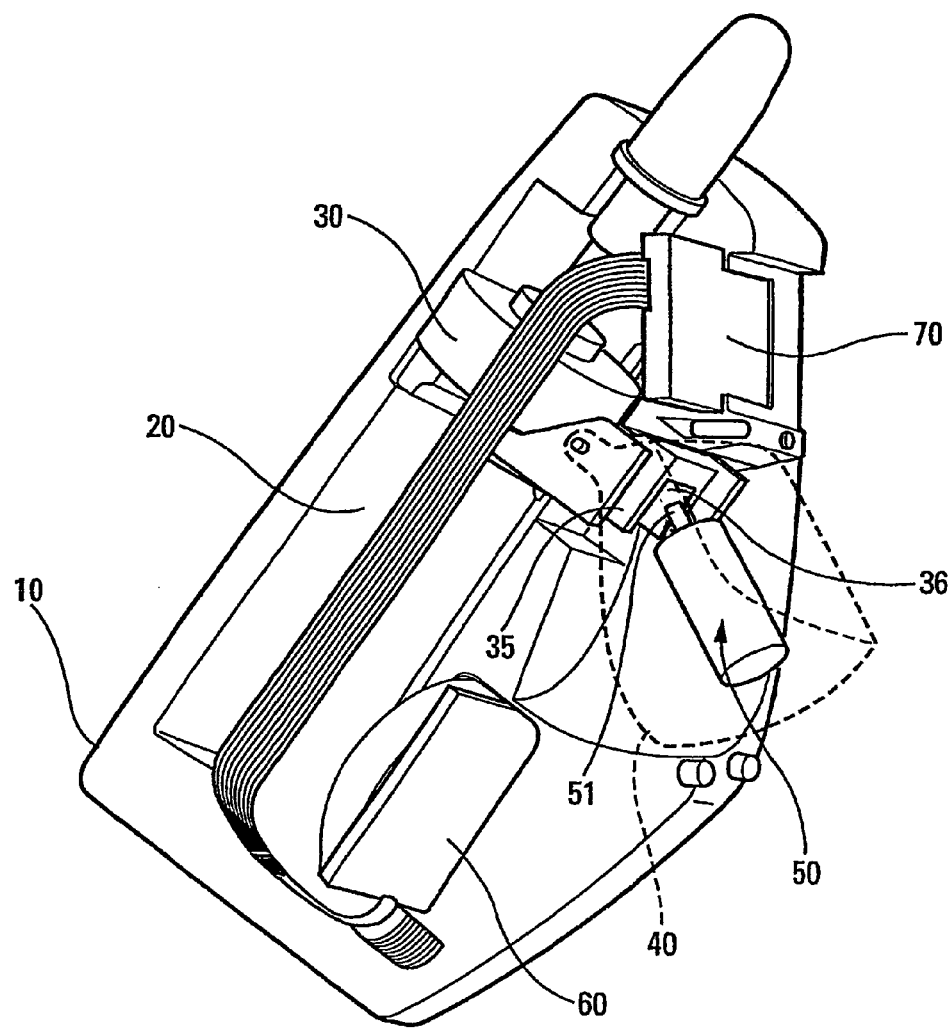

With reference more particularly to FIGS. 2A and 2B, the securing system 50 advantageously has a rod 51 which, in the clutched position, co-operates with an orifice 36 provided in a member 35 secured to the dispenser means 30. Said member 35 secured to the dispenser means 30 may be connected to the piston of the pump or to the valve member of the valve, or more generally to any portion of the dispenser means 30 generating the dispensing. The securing system 50, and more particularly the rod 51, is advantageously disposed inside the actuating button 40, as shown in FIG. 2A, in which the button is shown in dashed lines. In this way, the device may use a reservoir, a pump and an actuating system that are conventional, the presence of the securing system not requiring any particular modification of those elements, only the member 35 secured to the dispenser means 30, in particular the pump, being slightly modified to adapt to receiving the rod in the clutched position.

Advantageously, the device is provided with indicator means 70, and in particular an electronic LCD and/or sound alarms for informing the user of the state of the device and of the various functions of said device.

Figure 3:
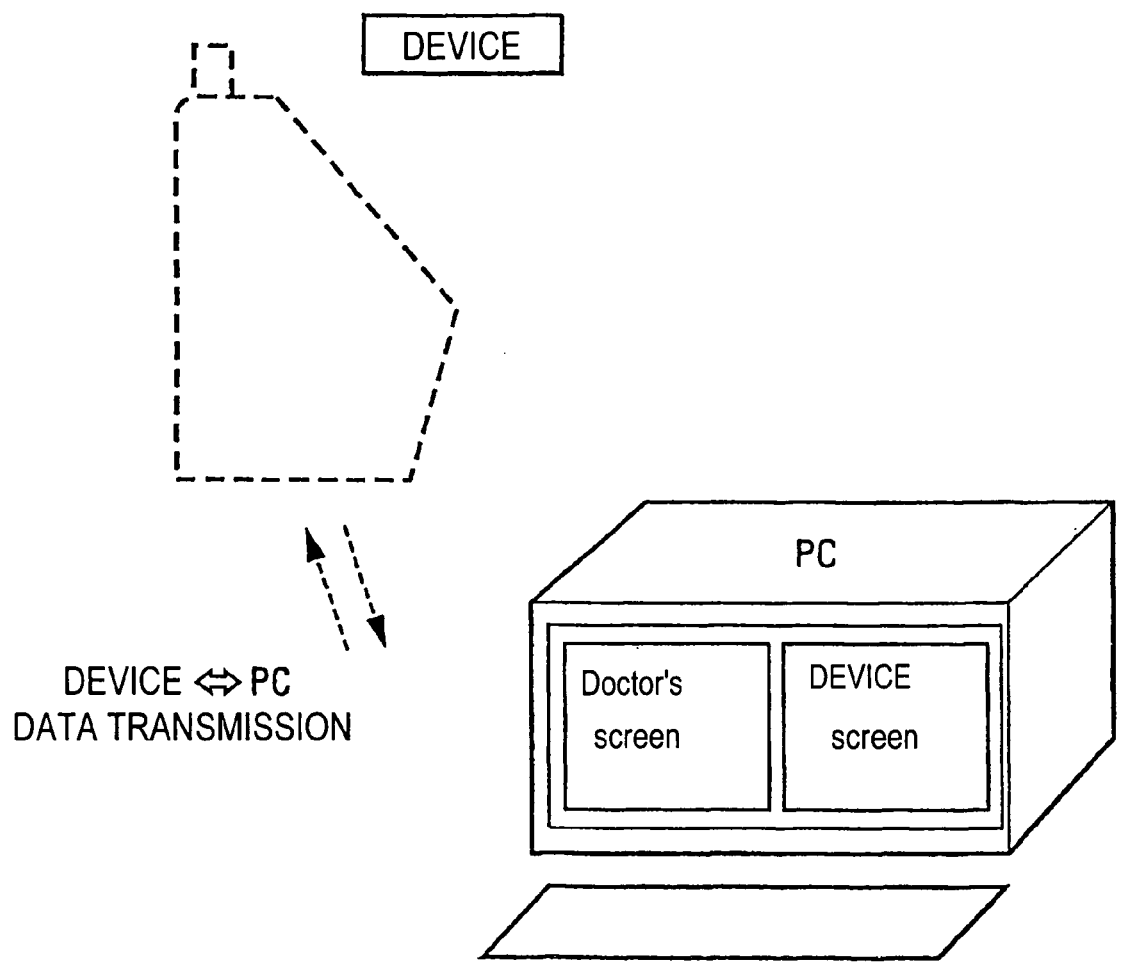
FIG. 3 is a diagram showing an advantageous use of the present invention.

As mentioned above, the control unit 60 is parameterizable, preferably remotely, so that the device has means for transmitting and receiving data. FIG. 3 diagrammatically shows such data transmission between a dispenser device and a personal computer (PC) which may be the doctor's computer. The parameters of the electronic control unit 60 can be modified, in particular by the doctor, and can be predetermined to perform a certain number of functions. Said functions may in particular comprise:

1. Instructions for using the apparatus: said instructions may be written in the electronic control unit of the device by means of the PC, and may include indications on the procedure for putting the device into service, length of treatment, dosage, etc.

2. First-time use indicator: the device may be made operational by peeling off a safety tab disposed, for example, between the battery and the control unit before the device is used for the first time. Once the tab is removed, the side actuator 40 is in a declutched position so that any actuation of said actuator does not cause any fluid or powder to be dispensed. This also guarantees safety in transit.

3. Priming the apparatus: the first time or the first times (in particular the first three times) the device is actuated may correspond to priming. This may be displayed on the LCD screen and color diodes may be provided on the device for the purpose of indicating to the user that the device is in a priming cycle.

4. Indicating to the patient when to take a dose: a signal, in particular a sound signal, may be emitted by the device together with a message which is displayed on the LCD screen of the device.

5. Displaying/storing the number of remaining doses: the number is stored in a memory in the control unit, and is displayed on the LCD of the device. In addition to displaying the number of doses remaining, it is possible to display the time remaining until the next dose is authorized to be taken. The device screen of the PC may also display the length of time of the treatment.

6. Automatic shutting down to standby mode: this can be set to occur after a certain number of minutes of not being used, it being possible to adjust that number by means of the PC. Such automatic shutting down to standby mode can concern in particular the diodes, the LCD, and the microprocessor.

7. Automatically coming out of standby mode: this can occur in two stages, namely firstly reactivating the display, and secondly requesting a code for operating the apparatus.

8. Possibility for the patient to take a dose after an authorized period, in the event that the patient forgets: if, for a given dosage, e.g. one dose every four hours (T0, T0+4, T0+8, etc.), dose T0+4 is forgotten, then it is possible for the patient to take that dose before time T0+8 (e.g. at T0+7). In which case, the timing (four hours between doses) is shifted to start running from the new time T0+7, i.e. T0+11, T0+15, etc. The timing may, in particular, be shifted by means of the PC.

9. Locking between dispensing of doses: the system is in the declutched position between dispensing of doses so as to prevent overdosage. The display on the device screen of the computer indicates the time remaining until the next dose is to be taken, which time is also displayed on the LCD of the device. A red diode may also light up during the locking period. The device may also be organized to require an unlocking code to be entered if necessary.

10. Checking that the device is positioned correctly while the dose is being dispensed: in order to guarantee an operating position of about 30° relative to the vertical axis, the device may prevent the pump from being actuated if the position is not correct, e.g. by means of an inclination-measuring sensor. In which case, a message may be displayed on the screen of the computer and/or on the screen of the device in order to warn the user that the position is incorrect.

11. Transmitting data to the doctor to determine the history of the dose-taking: the data stored in the device may be transmitted to the PC. The doctor can then have access to all of the information concerning the doses taken by the user of the device.

12. Modification of the dosage by the doctor: the time between doses may be modified by the doctor by means of the PC.

13. Warning the doctor that fewer than X doses remain in the apparatus: this may be achieved by being displayed on the doctor's screen of the PC, and the number of doses X from which such displaying occurs may be set by the PC. In addition, if a very few doses, e.g. five, remain, a message may be displayed on the device screen of the computer and/or on the LCD screen of the device, and the device may emit a strident sound by means of a sound alarm.

14. Child safety: access to the device may be regulated by a code (similar to the procedure for coming out of standby mode).

15. Making the system tamper-proof after the last dose has been dispensed (end of treatment): after it has been used for the last time, the device may be locked, and an indication to that effect may be displayed on the display of the device and on the display of the PC.

16. Possibility of refilling and recharging the prototype after it has been used for the last time: the reservoir may be refilled, and the battery may be recharged, and the various parameters may be reset by means of the PC.

Naturally, the above-described functions are given merely by way of example for a particular device, and various other functions may be considered, it being possible for other functions to be added easily to the device by using electronics.

The essential characteristic of the present invention lies in the simplicity of the securing means which are implemented merely by a single rod disposed inside the manual actuating button and clutching or declutching with a member that actuates the dispenser pump. This characteristic and this implementation make it possible to obtain a device that is comprehensive, that is transportable, that offers accurate and reproducible dosing, and that is electronically parameterizable without having to modify the components of the fluid or powder nasal or oral spray device itself, i.e. the reservoir, the pump, or the manual actuator element.

Although the present invention is described with reference to a particular embodiment thereof, clearly the person skilled in the art may make various modifications to that embodiment without going beyond the ambit of the present invention as defined by the accompanying claims.

The invention claimed is:

1. A fluid or powder nasal or oral spray device comprising a body (10), at least one fluid or powder reservoir (20) containing one or more doses of fluid or powder to be dispensed, manually actuated dispenser means (30), and a manual actuator element (40) actuated by manual pressure to cause said dispenser means (30) to dispense doses of fluid or powder, said device being characterized in that it further comprises a securing system (50) which is mounted to move between a clutched position, in which said manual actuator element (40) co-operates with said dispenser means (30), and a declutched position, in which said manual actuator element (40) does not co-operate with said dispenser means (30), said securing system (50) being controlled by a parameterizable electronic control unit (60).

2. A device according to claim 1, in which said securing system (50) comprises a mechanical element (51), mounted to move between a clutched position in which it mechanically connects said actuator element (40) to a member (35) secured to the dispenser means (30) so that actuating said actuator element (40) causes a dose of fluid or powder to be dispensed, and a declutched position in which there is no coupling between the actuator element (40) and the dispenser means (30), so that actuating said actuator element (40) does not caused any fluid or powder to be dispensed.

3. A device according to claim 2, in which said actuator element (40) is a button mounted to pivot or slide on one side of said body (10), in which said mechanical elements is a rod and said rod (51) is disposed in said actuating button (40), one end of said rod (51) co-operating with an orifice (36), when said rod (51) is in the clutched position, which orifice serves to receive said member (35) secured to the dispenser means (30).

4. The device according to claim 2, in which the mechanical element is a rod.

5. A device according to claim 1, in which said dispenser means (30) are implemented in the form of a pump or of a valve, said member (35) secured to the dispenser means (30) being connected to the piston of the pump, or to the valve member of the valve.

6. A device according to claim 1, in which said control unit (60) comprises a microprocessor and power supply means.

7. A device according to claim 1, in which said device further comprises indicator means (70) for informing the user of the state of the device.

8. A device according to claim 1, in which said control unit (60) can be parameterized remotely, in particular by means of a computer (PC), and further comprises means for transmitting and receiving data.

9. A device according to claim 1, in which said control unit (60) can be parameterized to enable and to inhibit actuation of the device through a plurality of predeterminable functions.

10. A device according to claim 9, in which said predeterminable functions comprise in particular access authorization, priming of the device, dosage of the fluid or powder contained in the reservoir, safety against overdosage, length of time of the treatment, shutting down to standby mode and coming out of standby mode, operating position, child safety and warning the patient's doctor.

11. A fluid or powder nasal or oral spray device, comprising:
a body,
a reservoir containing a fluid or a powder for dispensing into the nasal or oral cavity;
a pump or valve;
a manually operated actuator that operates the pump or valve to dispense doses of fluid or powder upon being manually depressed to apply pressure to the pump or valve; and a securing system mounted to move between a clutched position, in which the manually operated actuator co-operates with the pump or valve, and a declutched position, in which the manually operated actuator does not co-operate with the pump or valve, and wherein the securing system is controlled by a parameterizable electronic control unit.

12. The device according to claim 11, in which the manually operated actuator is a lever or button.

13. The device according to claim 11, wherein the securing system comprises a mechanical element mounted to move between a clutched position in which it mechanically connects the manually operated actuator to a member secured to the pump or valve so that actuating manually operated actuator causes a dose of fluid or powder to be dispensed, and a declutched position in which there is no coupling between the manually operated actuator and the pump or valve, so that actuating the manually operated actuator does not cause any fluid or powder to be dispensed.

14. The device according to claim 13, wherein the manually operated actuator is mounted to pivot or slide on one side of the body, and wherein the mechanical element is a rod disposed in the manually operated actuator, one end of the rod co-operating with an orifice, when the rod is in the clutched position, which orifice serves to receive the member secured to the pump or valve.

15. The device according to claim 11, wherein the control unit can be parameterized remotely to move the securing system to a declutched position to prevent manual actuation of the pump or valve.

* * * * *